United States Patent
MacArthur et al.

(10) Patent No.: US 11,389,315 B2
(45) Date of Patent: Jul. 19, 2022

(54) ORTHOTIC DEVICE RESPONSIVE TO DETECTED FORCES AT USER-OPERATED TOOL

(71) Applicants: Benjamin MacArthur, Barrie (CA); Jonathan Minto, Barrie (CA); Benjamin Adam Hoffman, Marysville, OH (US); Darrell Hastings, Mount Forest (CA); Angelica Gabrielle Trumpler, Mulmur (CA)

(72) Inventors: Benjamin MacArthur, Barrie (CA); Jonathan Minto, Barrie (CA); Benjamin Adam Hoffman, Marysville, OH (US); Darrell Hastings, Mount Forest (CA); Angelica Gabrielle Trumpler, Mulmur (CA)

(73) Assignee: HONDA MOTOR CO., LTD., Tokyo (JP)

( * ) Notice: Subject to any disclaimer, the term of this patent is extended or adjusted under 35 U.S.C. 154(b) by 1425 days.

(21) Appl. No.: 15/043,989

(22) Filed: Feb. 15, 2016

(65) Prior Publication Data
US 2017/0231792 A1 Aug. 17, 2017

(51) Int. Cl.
*A61F 5/00* (2006.01)
*A61F 5/01* (2006.01)
*A61F 5/058* (2006.01)

(52) U.S. Cl.
CPC .............. *A61F 5/012* (2013.01); *A61F 5/013* (2013.01); *A61F 5/05866* (2013.01); *A61F 2005/0181* (2013.01)

(58) Field of Classification Search
CPC .. A61F 5/012; A61F 5/04; A61F 5/042; A61F 5/048; A61F 5/0104; A61F 5/0106;
(Continued)

(56) References Cited

U.S. PATENT DOCUMENTS

| 2,312,523 A | 3/1943 | Corbett |
| 4,413,620 A | 11/1983 | Tucker |

(Continued)

FOREIGN PATENT DOCUMENTS

| CA | 2285053 A1 | 10/1998 |
| CA | 2321666 A1 | 9/1999 |

OTHER PUBLICATIONS

DG Industries, "DG Industries Ergonomic Products", http://www.dgindustries.com/Ergonomic_Products.htm, accessed on Dec. 9, 2015.
(Continued)

*Primary Examiner* — Victoria Hicks Fisher
(74) *Attorney, Agent, or Firm* — Armstrong Teasdale LLP

(57) ABSTRACT

An orthotic device is provided. The orthotic device is worn on an appendage of a user of a fastener installation tool, and is configurable between a relaxed state and a rigid state. The orthotic device includes at least one activation component that is responsive to an activation signal output by a controller in communication with the fastener installation tool. The activation component changes the orthotic device from the relaxed state to the rigid state in response to the controller detecting a resistive force at the fastener installation tool during installation of a fastener.

13 Claims, 3 Drawing Sheets

(58) Field of Classification Search
CPC .. A61F 5/0009; A61F 5/0118; A61F 5/05816; A61F 5/05841; A61F 5/0585; A61F 5/05858; A61F 5/013; A61F 5/05866; A61F 2005/0181; A61F 5/01
See application file for complete search history.

(56) References Cited

U.S. PATENT DOCUMENTS

| | | | |
|---|---|---|---|
| 5,885,036 A | 3/1999 | Wheeler | |
| 6,324,728 B1 | 12/2001 | Blankenheim | |
| 6,540,707 B1 | 4/2003 | Stark et al. | |
| 6,592,538 B1 | 7/2003 | Hotchkiss et al. | |
| 6,969,365 B2 | 11/2005 | Scorvo | |
| 7,513,881 B1 | 4/2009 | Grim et al. | |
| 7,641,668 B2 | 1/2010 | Perry et al. | |
| 7,740,602 B2 | 6/2010 | Christensen | |
| 8,005,651 B2 | 8/2011 | Summit et al. | |
| 8,613,716 B2 | 12/2013 | Summit et al. | |
| 8,784,350 B2 | 7/2014 | Cohen | |
| 9,931,701 B1 | 4/2018 | Klein et al. | |
| 2003/0018286 A1 | 1/2003 | Porrata et al. | |
| 2004/0092831 A1* | 5/2004 | Hood, Jr. | A61B 5/02225 600/490 |
| 2009/0070938 A1* | 3/2009 | Kell | A61F 5/05891 5/644 |
| 2011/0009757 A1* | 1/2011 | Sano | A61B 5/02233 600/499 |
| 2011/0054283 A1* | 3/2011 | Shuler | A61B 5/445 600/364 |
| 2012/0037386 A1 | 2/2012 | Cook | |
| 2012/0101418 A1* | 4/2012 | Manoach | A61F 5/05825 602/13 |
| 2013/0023741 A1* | 1/2013 | Ayanruoh | A61B 5/01 600/301 |
| 2014/0070042 A1 | 3/2014 | Beers et al. | |
| 2014/0142485 A1 | 5/2014 | Berry et al. | |
| 2015/0073322 A1 | 3/2015 | Cohen | |
| 2016/0354222 A1* | 12/2016 | Alsolami | A61F 5/012 |

OTHER PUBLICATIONS

DG Industries, "Biometric Brace", http://www.dgindustries.com/tour/tour-5.htm, accessed on Dec. 9, 2015.
DG Industries, "SideArm", http://www.dgindustries.com/tour-6.htm, accessed on Dec. 9, 2015.
DG Industries, "Bio-Brace 2.0", http://www.dgindustries.com/tour/tour-4.htm, accessed on Dec. 9, 2015.
DG Industries, "Bio-Brace Classic", http://www.dgindustries.com/tour/tour-1.htm, accessed on Dec. 9, 2015.
Stone, Andy, "Brace Yourself", Forbes, Oct. 26, 2007, 5 pages, http://www.forbes.com/forbes/2007/1112/104.html.
Non-Final Office Action dated Dec. 16, 2021 for U.S. Appl. No. 16/662,996; 30 pp.

* cited by examiner

ORTHOTIC DEVICE RESPONSIVE TO DETECTED FORCES AT USER-OPERATED TOOL

BACKGROUND

The present disclosure relates generally to orthotic devices and, more specifically, to adjustable orthotic devices responsive to detected resistive forces associated with a user-operated tool.

When using a hand-operated tool to install fasteners, such as bolts and screws, during the manufacture or maintenance of products, such as automobiles, at least some known tools may accumulate a resistive force (e.g., torque, friction), and impart the resistive force to an operator of the tool. For example, a direct-current (DC) powered tool configured to rotate a fastener at an installation point may accumulate torque generated by the fastener impacting or engaging the installation point. The accumulated resistive force may be at least partially transferred to an operator of the tool.

Repetitive fastener installations and the repetitive transfer of associated forces to the operator of a tool may cause the operator to experience ergonomic fatigue. In particular, the operator may experience ergonomic fatigue due to the repetitive resistive forces absorbed by their arm.

BRIEF SUMMARY

In one aspect, an orthotic device is provided. The orthotic device is configured to be worn on an appendage of a user of a fastener installation tool, and is configurable between a relaxed state and a rigid state. The orthotic device includes at least one activation component responsive to an activation signal output by a controller in communication with the fastener installation tool. The activation component changes the orthotic device from the relaxed state to the rigid state in response to the controller detecting a resistive force at the fastener installation tool during installation of a fastener.

In another aspect, an orthotic system is provided. The system includes a fastener installation tool for installing fasteners, a controller coupled to the fastener installation tool, and an orthotic device configured to be worn on an appendage of a user of the fastener installation tool. The controller detects a resistive force at the fastener installation tool during installation of a fastener, and outputs an activation signal in response to detecting the resistive force. The orthotic device is configurable between a relaxed state and a rigid state, and changes from the relaxed state to the rigid state in response to the activation signal output from the controller.

In yet another aspect, a method of operating an orthotic system is provided. The orthotic system includes a fastener installation tool, a controller coupled to the fastener installation tool, and an orthotic device configured to be worn on an appendage of a user of the fastener installation tool. The method includes detecting, using the controller, a resistive force at the fastener installation tool during installation of a fastener, outputting, using the controller, an activation signal in response to detecting the resistive force at the fastener installation tool, and changing the orthotic device from a relaxed state to a rigid state in response to the activation signal output from the controller.

DETAILED DESCRIPTION

The systems and methods described herein relate generally to orthotic devices and, more specifically, to adjustable orthotic devices that are responsive to detected resistive forces associated with a user-operated tool.

As described further herein, the orthotic devices of the present disclosure are configured to be coupled to an appendage (e.g., an arm, a hand, a wrist, etc.) of a user operating a tool. As resistive forces (e.g., torque or friction) are accumulated at the tool, a controller in communication with the tool causes the orthotic device to change from a relaxed state to a rigid state. While in the rigid state, the orthotic device substantially inhibits movement of the appendage coupled to the orthotic device to facilitate preventing the resistive forces from causing injury to the user. Once the accumulated resistive force reaches a desired level, the controller causes the orthotic device to change from the rigid state to the relaxed state to permit rotation and movement of the appendage.

Figure 1:
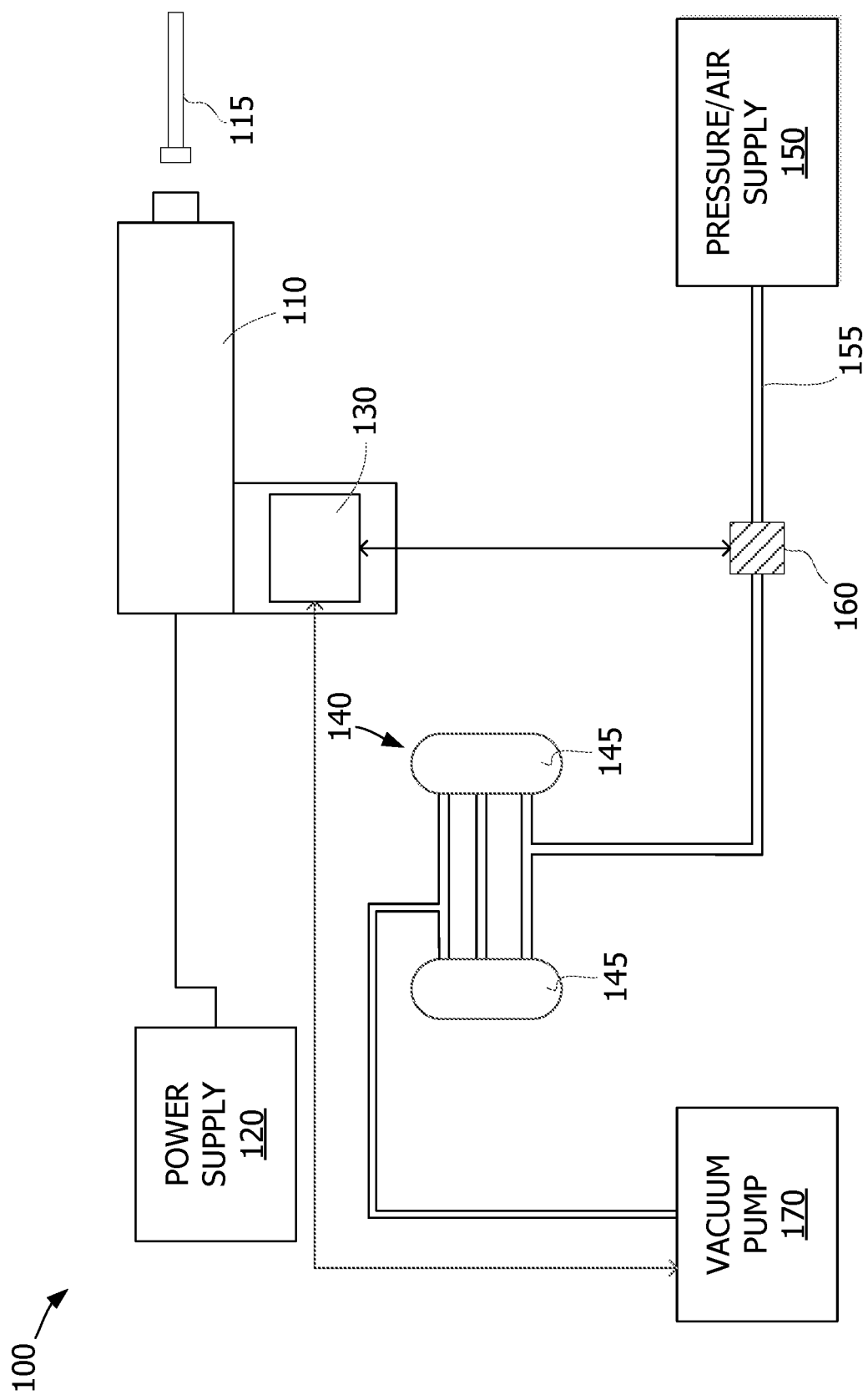
FIG. 1 is a block diagram of an exemplary orthotic system including an adjustable orthotic device.

FIG. 1 is a block diagram of an exemplary orthotic system 100. In the exemplary embodiment, system 100 includes a fastener installation tool 110, a power supply 120, a controller 130, an orthotic device 140, an air supply 150, a valve 160, and a vacuum pump 170. In other embodiments, system 100 may include additional, fewer, or alternative components, including those described elsewhere herein.

In the exemplary embodiment, fastener installation tool 110 is a direct-current (DC) powered tool that generates a reactive force when used to install a fastener, such as a bolt 115. Although fastener installation tool 110 is illustrated as being a right angle installation tool in the exemplary embodiment, fastener installation tool 110 may be any installation tool that enables system 100 to function as described herein. In some embodiments, for example, fastener installation tool 110 may be an in-line fastener installation tool. In other embodiments, fastener installation tool 110 may be a tool other than a DC powered tool, such as an alternating-current (AC) powered tool or a pneumatic tool. In the exemplary embodiment, fastener installation tool 110 is a hand-operated tool. In other embodiments, fastener installation tool 110 may be operated in a different configuration.

Fastener installation tool 110 is configured to install fasteners at installation sites, such as fastener openings defined in automotive frames or panels. In the exemplary embodiment, fastener installation tool 110 is used to install a bolt 115 at an installation site. Although fastener installation tool 110 is described herein with reference to bolt 115, it is understood that fastener installation tool 110 may be configured to install different types of fasteners, including, for example and without limitation, screws, rods, anchors, nails, pins, and the like.

In the exemplary embodiment, fastener installation tool 110 is coupled to power supply 120 to receive power. In the exemplary embodiments, power supply 120 is external to fastener installation tool 110. In other embodiments, power supply 120 may be integrally formed with fastener installation tool 110. In the exemplary embodiment, power supply 120 provides electrical energy to fastener installation tool 110 to generate mechanical energy, such as rotation, to install fasteners. Power supply 120 may be, for example, a DC voltage source, an AC voltage source, a battery, and/or a different component for generating and/or storing electrical energy. Alternatively, power supply 120 may provide a different type of energy. In one embodiment, for example, power supply 120 may be an air compressor or other source of compressed air. Energy provided by power supply 120 is converted to mechanical energy by fastener installation tool (e.g., rotation) to apply a force (e.g., torque) to bolt 115 during installation.

Controller 130 is communicatively coupled to fastener installation tool 110, and transmits and receives control signals to and from system 100 based on one or more operating parameters of fastener installation tool 110, as described in more detail herein. In the exemplary embodiment, controller 130 is integrated within fastener installation tool 110. In other embodiments, controller 130 may be separate from fastener installation tool 110 and may be communicatively coupled to fastener installation tool 110 via any suitable wired and/or wireless communications link.

In some embodiments, controller 130 includes and/or is communicatively coupled to one or more sensors (not shown) that monitor operation of fastener installation tool 110. In some embodiments, fastener installation tool 110 may include the one or more sensors, and may transmit a signal to controller 130 based on data collected by the sensors. In some embodiments, for example, fastener installation tool 110 includes a current sensor (e.g., a current transducer) configured to measure a magnitude of current supplied to fastener installation tool 110. Controller 130 may use the detected current to calculate or estimate the torque applied to bolt 115 and/or the resistive force imparted to fastener installation tool 110 from bolt 115.

Controller 130 may be any suitable controller that enables system 100 to function as described herein, including any suitable analog controller, digital controller, or combination of analog and digital controllers. In some embodiments, controller 130 includes a processor (not shown) that executes instructions for software loaded in a memory device. Controller 130 may generally include any suitable computer and/or other processing unit, including any suitable combination of computers, processing units and/or the like that may be operated independently, or in combination with one another. Thus, in several embodiments, controller 130 may include one or more processor(s) and associated memory device(s) configured to perform a variety of computer-implemented functions including, but not limited to, the functions disclosed herein, such as detecting a resistive force at fastener installation tool 110, outputting an activation signal to one or more components of system 100 in response to a sensed or detected resistive force at fastener installation tool 110, detecting a magnitude of torque applied to a fastener by fastener installation tool 110, and outputting a deactivation signal to one or more components of system 100 when the detected magnitude of torque is equal to a desired installation torque, in accordance with the processes and methods described herein.

As used herein, the term "processor" refers not only to integrated circuits, but also refers to a microcontroller, a microcomputer, a programmable logic controller (PLC), an application specific integrated circuit, and other programmable circuits. Additionally, the memory device(s) of controller 130 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) may generally be configured to store suitable computer-readable instructions that, when implemented by the processor(s), configure and/or cause the associated controller to perform various functions including, but not limited to, the functions described herein.

During installation, in the exemplary embodiment, fastener installation tool 110 applies a torque (i.e., rotational force) or other force to bolt 115 to drive bolt 115 into the installation site. Bolt 115 may produce a reactionary resistive force, such as torque or friction, induced to fastener installation tool 110 during installation of each bolt 115. More specifically, as bolt 115 is rotated, force applied by fastener installation tool 110 and the resistive force produced by bolt 115 may be accumulated at fastener installation tool 110. At least some of the accumulated torque may be transferred to a user of tool 110 during installation.

In the exemplary embodiment, orthotic device 140 is coupled to at least one appendage or joint of the user to which resistive forces from fastener installation tool 110 may be transferred. Orthotic devices described herein are particularly suitable for coupling to the arm, specifically, the forearm, of a user. As used herein, "arm" may refer any portion of the user from the shoulder to the hand of the user. Alternatively, the orthotic devices described herein may be coupled to a different appendage or body part, such as a leg or the torso of the user. Orthotic device 140 is variably positioned between a relaxed state, in which orthotic device 140 permits rotational and lateral movement of the user's appendage or joint, and a rigid state, in which orthotic device 140 is configured to displace or distribute resistive forces from fastener installation tool 110 to facilitate preventing ergonomic fatigue in the appendage or joint coupled to orthotic device 140. In at least some embodiments, orthotic device 140 may be variably positioned to one or more intermediate states defined between the relaxed and rigid states. In the exemplary embodiment, before fastener installation tool 110 is operated, orthotic device 140 is selectively positioned in the relaxed state.

Controller 130 senses or detects a resistive force at fastener installation tool 110 during installation of bolt 115. In particular, controller 130 detects a magnitude of an accumulated resistive force and/or a current (i.e., instantaneous) resistive force. In some embodiments, controller 130 calculates or estimates the resistive force based on a magnitude of current supplied to fastener installation tool 110. In response to the detected resistive force, controller 130 outputs an activation signal that causes orthotic device 140 to change from the relaxed state to the rigid state to enable orthotic device 140 to distribute and/or displace resistive forces imparted to a user's appendage from fastener installation tool 110. In some embodiments, one or more threshold values may be stored in controller 130 (e.g., stored in one or memory devices of controller 130), and controller 130 may be programmed to compare the detected resistive forces to the one or more threshold values, and to transmit the activation signal when a detected resistive force exceeds one or more threshold values. In certain embodiments, controller 130 may transmit an activation signal to cause orthotic device 140 to change to an intermediate state in response to the detected resistive force.

In some embodiments, controller 130 is further configured to output a deactivation signal that causes orthotic device 140 to change from the rigid state to the relaxed state. In one embodiment, for example, controller 130 outputs a deactivation signal that causes orthotic device 140 to change from the rigid state to the relaxed state when a fastener is installed with a desired installation torque. Controller 130 may detect a final or the last magnitude of torque applied to a fastener by fastener installation tool 110, and output a deactivation signal when the final magnitude of torque is equal to a desired installation torque. Values for desired installation torques may be stored, for example, in one or more memory devices of controller 130.

Controller 130 may compare the magnitude of the final torque applied to a fastener prior to cessation of a fastener installation process to the desired installation torque to determine if the fastener has been installed at the desired installation torque. For example, when the user stops installing bolt 115, controller 130 detects the magnitude of the last torque applied to bolt 115, and compares that magnitude to the desired installation torque to determine if bolt 115 is installed at the desired installation torque. If the magnitude is equal to the desired installation torque, controller 130 outputs the deactivation signal to change orthotic device 140 from the rigid state to the relaxed state. If the magnitude is not equal to the desired installation torque, controller 130 does not output the deactivation signal, and orthotic device 140 is maintained in the rigid state.

In the exemplary embodiment, orthotic device 140 includes one or more bladders 145 (generally, an "activation component") responsive to the activation and deactivation signals output by controller 130. Specifically, in the exemplary embodiment, bladders 145 are selectively inflated and deflated in response to the activation and deactivation signals, respectively, output by controller 130 to modulate orthotic device between the rigid and relaxed states. Bladders 145 receive a fluid, such as air, to cause orthotic device 140 to inflate into the rigid state. Controller 130 controls the state of orthotic device 140 by regulating the delivery and removal of fluid to and from bladders 145 of orthotic device 140. Alternatively, orthotic device 140 may be configured to change between the relaxed state and the rigid state using a different configuration. Further, while orthotic device 140 is described with reference to bladders 145 in the exemplary embodiment, orthotic device 140 may include activation components other than bladders, for example, but not limited to, a magnetorheological fluid system, an electrorheological fluid system, and/or any other material or system that allows orthotic device 140 to function as described herein.

In the exemplary embodiment, air supply 150 is coupled in fluid communication with bladders 145 of orthotic device 140 through a fluid conduit 155. Air supply 150 provides fluid, such as air, to bladders 145 of orthotic device 140. Air supply 150 may include, for example and without limitation, a compressed air tank, a pump, or a compressor. In certain embodiments, air supply 150 may be electrically coupled to power supply 120. Air supply 150 may be communicatively coupled to controller 130 to enable controller 130 to selectively adjust one or more operating parameters (e.g., motor speed, voltage, current, etc.) to regulate the supply of air to orthotic device 140.

Valve 160 is fluidly coupled between orthotic device 140 and air supply 150, and selectively regulates the supply of air from air supply 150 to orthotic device 140. In one embodiment, valve 160 is integrated with orthotic device 140 and/or is directly coupled to one of bladders 145 (i.e., without an intervening conduit or hose). In another embodiment, valve 160 is integrated with air supply 150. In the exemplary embodiment, valve 160 is an electrically-actuated valve, such as a solenoid valve, and is actuated by control signals transmitted by controller 130. For example, the activation and deactivation signals output by controller 130 cause valve 160 to actuate between an open position and a closed position, respectively. When valve 160 is opened, air from air supply 150 inflates bladders 145 of orthotic device 140. When valve 160 is closed, air flow to bladders 145 from air supply 150 is blocked. In other embodiments, valve 160 may be any suitable type of valve that enables system 100 to function as described herein.

Vacuum pump 170 is coupled in fluid communication with bladders 145 of orthotic device 140 to facilitate removal of air or other fluid from orthotic device 140 to change orthotic device 140 from the rigid state to the relaxed state. In some embodiments, vacuum pump 170 may be coupled to power supply 120. Vacuum pump 170 is communicatively coupled to controller 130 and/or valve 160 to detect a deactivation signal output by controller 130. Vacuum pump 170 is activated in response to receiving the deactivation signal from controller 130 and/or detecting the deactivation signal being output by controller 130. When activated, vacuum pump 170 generates a reduced or negative pressure at one or more outlets of bladders 145 to deflate orthotic device 140 and change orthotic device 140 from the rigid state to the relaxed state. In some embodiments, vacuum pump 170 can deflate orthotic device 140 to an intermediate state. In some embodiments, vacuum pump 170 and air supply 150 may be integrally formed and/or may be fluidly connected as part of a closed fluid circuit.

Figure 2:
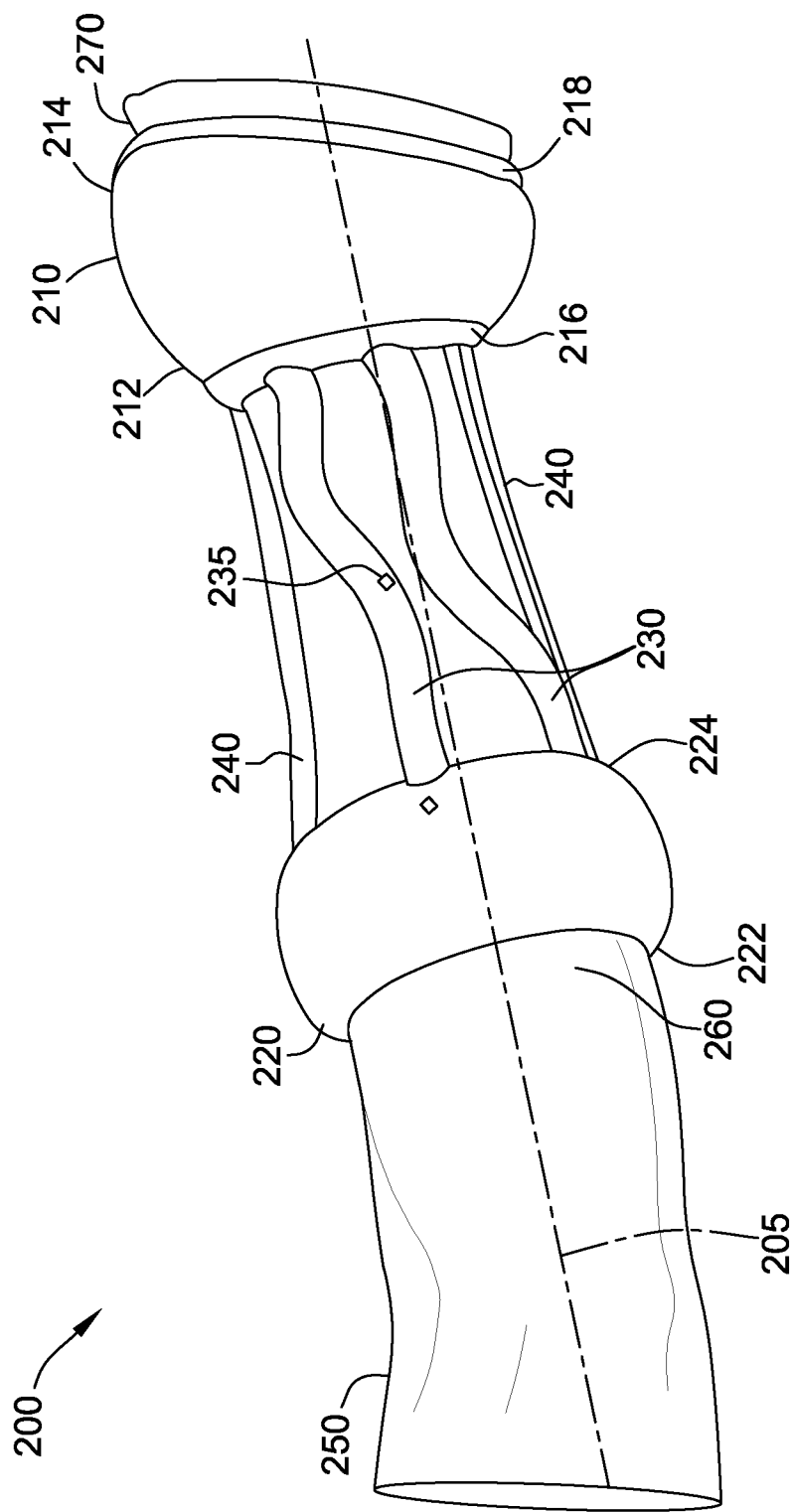
FIG. 2 is a perspective view of an exemplary orthotic device that may be used in the orthotic system shown in FIG. 1.

FIG. 2 is a perspective view of an exemplary orthotic device, shown in the form of an arm brace 200, suitable for use in system 100 (shown in FIG. 1). In the exemplary embodiment, device 200 includes a first bladder 210, a second bladder 220, fluid conduits 230, and braces 240. In other embodiments, device 200 may include additional, fewer, or alternative components or configurations. For example, device 200 may be configured to attach to a different appendage of the user.

In the exemplary embodiment, device 200 couples to an arm 250 of the user. In particular, device 200 is attached to arm 250 when the user is operating a fastener installation tool (e.g., tool 110, shown in FIG. 1) with arm 250. First bladder 210 is configured (e.g., sized and shaped) to be coupled about the wrist of arm 250. Second bladder 220 is configured (e.g., sized and shaped) to be coupled about a forearm 260 of arm 250 and is spaced apart from first bladder 210. In other embodiments, first bladder 210 and second bladder 220 may be positioned and/or coupled at different locations along arm 250. In one embodiment, for example, second bladder 220 is coupled around the elbow of arm 250. Fluid conduits 230 and braces 240 extend between first bladder 210 and second bladder 220, and are circumferentially-spaced about a longitudinal centerline 205 of device 200 to enable device 200 to be inserted onto arm 250.

In the exemplary embodiment, first bladder 210 and second bladder 220 are each an annular or ring-shaped bladder that defines a central opening that is sized and shaped to receive at least a portion of arm 250 therein. First bladder 210 and second bladder 220 are fabricated from a suitably flexible or semi-flexible material (e.g., rubber or plastic) to enable inflation and deflation. In the exemplary embodiment, first bladder 210 includes a first or proximal side 212 sized to fit about the wrist of arm 250, and a second or distal side 214 that is sized to fit about the base of a hand 270 of arm 250. As used herein, "proximal" refers to a direction extending towards the torso of a body (e.g., towards a shoulder of arm 250) and "distal" refers to a direction extending away from the torso of the body (e.g., towards hand 270). The opening defined by first bladder 210 is smaller at proximal side 212 than at distal side 214 to facilitate securely fitting around the wrist of arm 250 and the base of hand 270. In the exemplary embodiment, the opening defined by second bladder 220 has a substantially constant diameter, although in other embodiments, the opening defined by second bladder 220 may be tapered from a proximal side 222 of second bladder 220 to a distal side 224 of second bladder 220.

In the exemplary embodiment, device 200 includes a first support ring 216 and a second support ring 218. First support ring 216 is coupled to proximal side 212 of first bladder 210 and second support ring 218 is coupled to distal side 214 of first bladder 210. First support ring 216 and second support ring 218 are constructed from a rigid or semi-rigid material and are sized and shaped to fit arm 250. In some embodiments, first support ring 216 and second support ring 218 are formed integrally with first bladder 210 (e.g., by an additive manufacturing process). When first bladder is inflated, first bladder 210 biases second support ring 218 away from first support ring 216 and into engagement with the base of hand 270 to substantially inhibit rotation of hand 270 relative to forearm 260.

Fluid conduits 230 extending from first bladder 210 to second bladder 220 are circumferentially-spaced around longitudinal centerline 205. When device 200 is coupled to arm 250, fluid conduits 230 are circumferentially-spaced around arm 250 as well. Fluid conduits 230 are constructed from rigid or semi-rigid materials, and may facilitate limiting rotation of first bladder 210 relative to second bladder 220. Fluid conduits 230 fluidly couple first bladder 210 and second bladder 220 such that inflating either of first bladder 210 or second bladder 220 causes the other of first bladder 210 and second bladder 220 to inflate. Similarly, deflating either of first bladder 210 or second bladder 220 causes the other of first bladder 210 and second bladder 220 to deflate. In other embodiments, fluid conduits 230 may permit inflation and/or deflation of first bladder 210 and second bladder 220 asymmetrically and/or asynchronously. In one embodiment, for example, fluid conduits 230 are configured such that first bladder 210 deflates only after second bladder 220 has deflated. Although two fluid conduits 230 are illustrated in the exemplary embodiment, device 200 may include any number of fluid conduits 230 that enables device 200 and/or system 100 to function as described herein. In some embodiments, for example, device 200 may include a single (i.e., only one) fluid conduit 230.

Braces 240 extend from first bladder 210 to second bladder 220, and are circumferentially-spaced around longitudinal centerline 205. Braces 240 are constructed from suitably rigid materials and provide a relatively rigid mechanical link between first bladder 210 and second bladder 220 such that braces 240 transmit rotational forces (e.g., rotational forces imparted to hand 270 from a fastener installation tool) from first bladder 210 to second bladder 220. The exemplary embodiment includes two braces 240 coupled to diametrically-opposed sides of device 200. In other embodiments, device may include more or less than two braces. In some embodiments (e.g., where a joint of arm 250 is between first bladder 210 and second bladder 220), fluid conduits 230 and/or braces 240 may be hinged to permit movement of a joint of arm 250.

Device 200 includes one or more fluid inlet and outlet ports for coupling to a fluid supply and/or a pump (e.g., air supply 150 and vacuum pump 170, shown in FIG. 1) for inflating and deflating first bladder 210 and second bladder 220. In the exemplary embodiment, a single fluid port, shown in the form of an opening 235, is formed on one of fluid conduits 230, though fluid ports may be located along any other portion of device 200 that enables fluid flow into and/or out of first bladder 210 and/or second bladder 220. In some embodiments, first bladder 210 includes either a fluid inlet port or a fluid outlet port, and second bladder includes the other of a fluid inlet port or a fluid outlet port. In other embodiments, one fluid conduit 230 includes a fluid inlet port, and another of fluid conduit 230 includes a fluid outlet port. In yet other embodiments, at least one fluid port is formed on either first support ring 216 and/or second support ring 218. The fluid ports include a suitable coupling structure to permit coupling to fluid conduits, such as fluid conduit 155 (shown in FIG. 1). In some embodiments, device 200 may include a single fluid port that acts as both a fluid inlet and a fluid outlet. In yet other embodiments, device 200 includes separate fluid inlet and outlet ports.

When device 200 is in the relaxed state (i.e., when first bladder 210 and second bladder 220 are deflated), device 200 permits unrestricted movement and rotation of arm 250, forearm 260, and hand 270. When device 200 is in the rigid state (i.e., when first bladder 210 and second bladder 220 are inflated, shown in FIG. 2), device 200 restricts movement and rotation of arm 250, and more specifically, relative movement and rotation of forearm 260 and hand 270. In particular, first bladder 210 and second bladder 220 restrict movement of the wrist of arm 250 and hand 270 to prevent injuries from resistive forces at the fastener installation tool. Resistive forces may cause the wrist and/or hand 270 to rotate, bend, or otherwise move in a manner that may induce or cause injury to a user. By inflating and restricting joint movement, first bladder 210 and second bladder 220 may facilitate reduced movement of arm 250 from resistive forces and reduced injuries associated with the resistive forces. In addition to restricting movement of arm 250, device 200 distributes or displaces the resistive forces and rotational forces at, for example, the wrist or hand to device 200 and/or another portion of arm 250, such as forearm 260. Distributing the resistive forces facilitates reduced stress or strain at a particular portion of arm 250.

More specifically, when first bladder 210 is inflated, first support ring 216 and second support ring 218 are biased away from one another and into engagement the wrist and hand 270, respectively, thereby inhibiting bending of hand 270 about the wrist. Moreover, when second bladder 220 is inflated, rotation of device 200 relative to arm 250 is inhibited such that rotational forces imparted on hand 270 from an external source (e.g., fastener installation tool 110) are transmitted and distributed across a larger and more massive portion of arm 250, such as forearm 260. More specifically, rotational forces imparted to hand 270 from a fastener installation tool are transferred to device 200 at first bladder 210, which are transmitted to second bladder 220 through braces 240. Such rotational forces are imparted to arm 250 through second bladder 220 because rotation of device 200 relative to arm 250 is substantially inhibited when device 200 is in the rigid state (i.e., when first bladder 210 and second bladder 220 are inflated). Device 200 thereby transmits and distributes rotational forces imparted on hand 270 across a larger and more massive portion of arm 250 to facilitate injury prevention and reducing user fatigue.

In the exemplary embodiment, device 200 is custom fitted to arm 250 to facilitate secure coupling between device 200 and arm 250. Any suitable method may be employed to custom fit device 200 to a user. In one embodiment, for example, the user's arm 250 is scanned (e.g., with a 3-D imaging system) and, based on the scan and/or other measurements of arm 250, components of device 200 are suitably sized and shaped to fit securely around arm 250. In at least some embodiments, one or more components of device 200 are fabricated using additive manufacturing techniques (also referred to as three-dimensional (3D) printing). In some embodiments, device 200 may be unitarily formed using additive manufacturing techniques to facilitate on-demand production for new users and reduce assembly time and costs.

Figure 3:
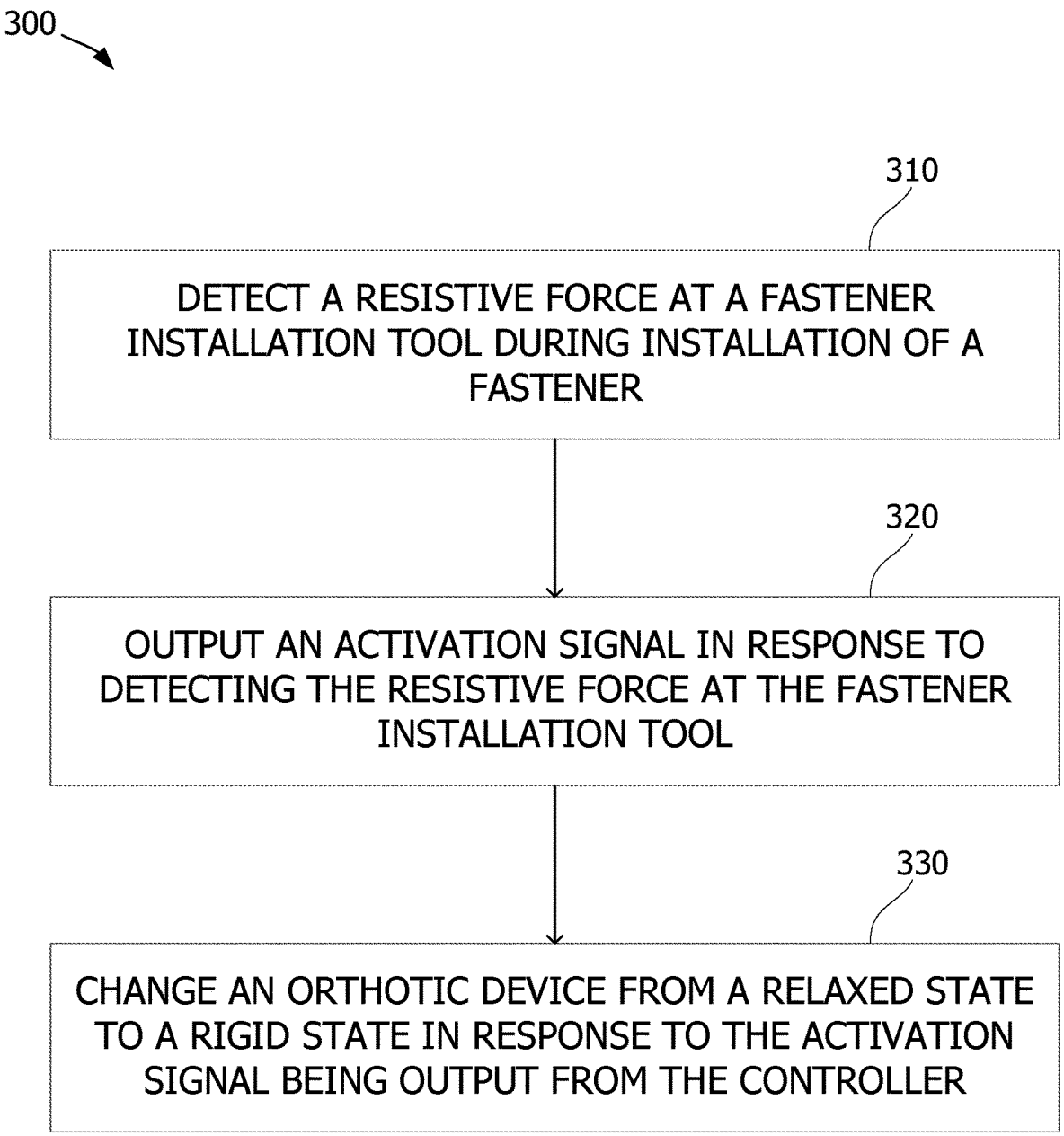
FIG. 3 is a flow diagram of an exemplary method of operating an orthotic device in the orthotic system shown in FIG. 1.

FIG. 3 is a flow diagram of an exemplary method 300 of operating an orthotic system (e.g., system 100, shown in FIG. 1) including a fastener installation tool, a controller coupled to the fastener installation tool, and an orthotic device configured to be worn on an arm of a user of the fastener installation tool. In other embodiments, method 300 includes additional, fewer, or alternative steps, including those described elsewhere herein.

Method 300 begins with the controller detecting 310 a resistive force at the fastener installation tool during installation of a fastener. In some embodiments, the controller detects 310 a resistive force that exceeds a threshold value. The controller outputs 320 an activation signal in response to detecting the resistive force at the fastener installation tool. In the exemplary embodiment, the activation signal is received by a valve coupled between a fluid supply and the orthotic device that opens and closes in response to control signals from the controller. In response to the activation signal being output from the controller, the orthotic device changes 330 from a relaxed state to a rigid state to restrict rotational movement of the arm and to distribute forces imparted to the arm of a user from the fastener installation tool. In at least some embodiments, the orthotic device includes at least one bladder. In, such embodiments, changing 330 the orthotic device from the relaxed state to the rigid state includes inflating the bladder by opening the valve to permit fluid flow from the fluid supply into the bladder. In the exemplary embodiment, when the controller detects that a fastener is installed with a desired installation torque, the controller outputs a deactivation signal that causes the orthotic device to change from the rigid state to the relaxed state. Specifically, in the exemplary embodiment, the controller outputs a deactivation signal that closes the valve to stop the flow of fluid to the at least one bladder, and activates a vacuum pump to facilitate removal of fluid from the at least one bladder.

The systems and methods described herein facilitate preventing injuries and reducing fatigue of operators operating tools, such as fastener installation tools. In particular, embodiments of the orthotic systems and methods described herein include an orthotic device that is switched between relaxed and rigid states based on resistive forces detected at the fastener installation tool. The orthotic device is configured to permit free movement of an appendage when there is no resistive force detected, and to restrict movement of the appendage when a resistive force is detected to prevent injuries and reduce fatigue. Activating the orthotic device based on detected resistive forces at a fastener installation tool provides an improvement over other orthotic devices that rely on detection of user movement to modify a state of the orthotic device. In particular, detected resistive forces at the fastener installation tool provide an earlier and more accurate indication of when a user's arm will be subjected to rotational forces from the fastener installation tool as compared to devices that rely on detected user movement. Embodiments of the systems and method described herein thereby enable more responsive and faster acting orthotic devices. In addition, manufacturing customized orthotic devices for each user with additive manufacturing techniques facilitates comfortable and correct fitting for a user and on-demand production of the orthotic device.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An orthotic system comprising:
a rotary fastener installation tool for installing fasteners;
a controller coupled to said rotary fastener installation tool and configured to:
detect one or more operating parameters of said rotary fastener installation tool; and
output an activation signal based on the one or more operating parameters of said rotary fastener installation tool; and
an orthotic device configured to be worn on an appendage of a user of said rotary fastener installation tool, said orthotic device configurable between a relaxed state and a rigid state, wherein said orthotic device changes from the relaxed state to the rigid state in response to the activation signal output from said controller, and wherein, in the rigid state, said orthotic device is configured to inhibit rotational movement of the appendage in response to reactive forces generated by said rotary fastener installation tool and applied to the appendage during installation of a fastener of the fasteners, the fasteners being discrete from the orthotic device.

2. The orthotic system of claim 1, wherein said orthotic device comprises at least one bladder configured to be worn around the appendage of the user of said rotary fastener installation tool, wherein said at least one bladder is inflated in response to the activation signal output from said controller.

3. The orthotic system of claim 2 further comprising:
an air supply; and
an electrically-actuated valve coupled between said air supply and said at least one bladder and configured to control supply of air into said at least one bladder, wherein said electrically-actuated valve is communicatively coupled to said controller and configured to open in response to receiving the activation signal from said controller.

4. The orthotic system of claim 3 further comprising a pump fluidly coupled to said at least one bladder for deflating said at least one bladder, wherein said pump is communicatively coupled to said controller and configured to deflate said at least one bladder in response to receiving a deactivation signal from said controller.

5. The orthotic system of claim 2, wherein said at least one bladder comprises a first bladder coupleable around a wrist of the user and a second bladder coupleable around a forearm of the user, wherein said first bladder is spaced apart from said second bladder and coupled to said second bladder by at least one brace configured to transmit rotational forces from said first bladder to said second bladder.

6. The orthotic system of claim 5, wherein said first bladder is fluidly coupled to said second bladder by at least one fluid conduit such that inflation of said first bladder results in inflation of said second bladder.

7. The orthotic system of claim 1, wherein said controller is further configured to detect a magnitude of torque applied the a fastener by said rotary fastener installation tool.

8. The orthotic system of claim 7, wherein said controller is configured to output a deactivation signal when the magnitude of torque detected by said controller is equal to a desired installation torque, and wherein said orthotic device changes from the rigid state to the relaxed state in response to the deactivation signal.

9. The orthotic system of claim 1, wherein said rotary fastener installation tool is a direct-current powered rotary tool.

10. The orthotic system of claim 1, wherein said controller is integrated within said rotary fastener installation tool.

11. A method of operating an orthotic system including a rotary fastener installation tool, a controller coupled to the rotary fastener installation tool, and an orthotic device configured to be worn on an appendage of a user of the rotary fastener installation tool, said method comprising:

detecting, using the controller, one or more operating parameters of the rotary fastener installation tool;
  outputting, using the controller, an activation signal based on the one or more operating parameters of the rotary fastener installation tool; and
  changing the orthotic device from a relaxed state to a rigid state in response to the activation signal output from the controller, wherein, in the rigid state, the orthotic device is configured to inhibit rotational movement of the appendage in response to reactive forces generated by the rotary fastener installation tool and applied to the appendage during installation of a fastener, wherein the fastener is discrete from the orthotic device.

12. The method of claim 11, wherein the orthotic device includes at least one bladder configured to be worn around the appendage of the user of the rotary fastener installation tool, wherein changing the orthotic device from the relaxed state to the rigid state comprises inflating the at least one bladder in response to the activation signal output from the controller.

13. The method of claim 12 further comprising:

detecting, using the controller, a magnitude of torque applied to a fastener by the rotary fastener installation tool; and
  deflating the at least one bladder when the magnitude of torque detected using the controller is equal to a desired installation torque.

* * * * *